United States Patent [19]

Tanaka et al.

[11] Patent Number: 5,110,982
[45] Date of Patent: May 5, 1992

[54] PROCESS FOR PRODUCING 2,6-NAPTHALENE DICARBOXYLIC ACID

[75] Inventors: Toru Tanaka; Masato Inari, both of Okayama, Japan

[73] Assignee: Mitsubishi Gas Chemical Company, Inc., Tokyo, Japan

[21] Appl. No.: 645,798

[22] Filed: Jan. 25, 1991

[30] Foreign Application Priority Data

Jan. 26, 1990 [JP] Japan .................. 2-17110
Feb. 6, 1990 [JP] Japan .................. 2-25074
Feb. 15, 1990 [JP] Japan .................. 2-32416

[51] Int. Cl.$^5$ .................................. C07C 51/265
[52] U.S. Cl. .............................. 562/414; 562/416; 562/488
[58] Field of Search ................. 562/416, 414, 488

[56] References Cited

U.S. PATENT DOCUMENTS 3,856,858 12/1974 Dighe et al. ............... 564/83
4,764,638 8/1988 Feld .......................... 562/416
4,886,906 12/1989 Tanaka et al. ............. 562/416

FOREIGN PATENT DOCUMENTS 73-34153 5/1973 Japan .
85-89445 5/1985 Japan .
87-61946 3/1987 Japan .
87-67048 3/1987 Japan .

Primary Examiner—Jose G. Dees
Assistant Examiner—Vera C. Clarke
Attorney, Agent, or Firm—Venable, Baetjer, Howard & Civiletti

[57] ABSTRACT

A process for producing 2,6-naphthalene dicarboxlic acid which comprises oxidizing a 2-alkyl-6-acyl naphthalene with molecular oxygen-containing gas in the presence of a catalyst containing cobalt, manganese and bromine in an acetic acid solvent, characterized in that the oxygen concentration in the exhaust gas is controlled so as to satisfy the following equation:

$$15/(X+7.5)+0.1 \leq Y \leq 90/(X+8)+0.4 \qquad (1)$$

wherein Y is oxygen concentration (volume %) in the exhaust gas and X (cm) is a distance between the inlet for an oxygen gas and the surface of the reaction solution in a static state, and the catalyst further contains an aromatic acid in which at least two carboxylic acid groups are in an orthposition or its precursor as a co-catalyst, and that part of all of the mother liquor from which the 2,6-naphthalene dicarboxylic acid crystal has been separated is cooled to remove the precipitated impurities, and thereafter is reused in the oxidation reaction, is disclosed.

6 Claims, 1 Drawing Sheet

PROCESS FOR PRODUCING 2,6-NAPTHALENE DICARBOXYLIC ACID

BACKGROUND OF THE INVENTION

This invention relates to a process for producing 2,6-naphthalene dicarboxylic acid (hereinunder referred to as 2,6-NDA) which is useful as a raw material for high quality polyester.

2,6-NDA has been worthy of notice as a raw material for high quality polyester having excellent thermal resistance, mechanical strength, dimensional accuracy and the like. Development of a commercial process for producing 2,6-NDA has been much in demand.

Prior arts on the production of 2,6-NDA are generally of the following three types.

(1) Processes for producing 2,6-NDA which comprise oxidizing 2,6-dimethyl naphthalene in the presence of a catalyst comprising a heavy metal and a bromine compound are disclosed in U.S. Pat. No. 3,856,855 and Japanese Patent Publication (Kokai) No. 34153/1973. In these processes, it is difficult to separate the raw material, 2,6-dimethyl naphthalene from the dimethyl naphthalene mixtures, and the amount of 2,6-dimethyl naphthalene separated is not sufficient.

(2) A process for producing 2,6-NDA which comprises oxidizing 2,6-diisopropyl naphthalene in the presence of a catalyst comprising Co and Mn is disclosed in Japanese Patent Publication (Kokoku) No. 89445/1985. Though 2,6-diisopropyl naphthalene can be easily synthesized, this process involves use of an excessive amount of the catalyst. So this process is not proper from an industrial point of view.

(3) Processes for producing 2,6-NDA which comprise oxidizing a 2-alkyl-6-acyl naphthalene in the presence of a catalyst containing Co and Mn or Co, Mn and Br are disclosed in Japanese Patent Publication (Kokai) Nos. 61946/1987 and 67048/1987 and U.S. Pat. No. 4,764,638. However, the yield of 2,6-NDA is insufficient in these processes.

Advantageously, 2-alkyl-6-acyl naphthalenes can be easily obtained in a high selectivity by Friedel Crafts Reaction between commercially available 2-methyl naphthalene and acetyl fluoride or butyryl fluoride. Therefore, 2-alkyl-6-acyl naphthalenes have became remarkable as a raw material for 2,6-NDA.

The present inventors have produced crude 2-methyl-6-butyryl naphthalene from 2-methyl naphthalene, propylene, carbon monoxide and hydrogen fluoride, or crude 2-methyl-6-acetyle naphthalene from 2-methyl naphthalene and acetyle fluoride, and purified the products. Then, the inventors have attempted the production of 2,6-NDA from 2-methyl-6-butyryl naphthalene or 2-methyl-6-acetyle naphthalene by oxidation under conditions which were known to be obtain high yields of 2,6-NDA from 2-methyl-6-acyl naphthalene in the prior art. However, high yields cannot be obtained from 2-methyl-6-butyryl naphthalene or 2-methyl-6-acetyle naphthalene under these conditions.

The present inventors conducted research on the production of 2,6-NDA from a 2-alkyl-6-acyl naphthalene by referring to references disclosing the process 2-methyl-6-acyl naphthalene as a raw material. However, satisfactory results could not be obtained. U.S. Pat. No. 4,886,906 dated Dec. 12, 1989 assigned to the assignee of this application discloses a process for producing 2,6-NDA which comprises oxidizing a 2-alkyl-6-acyl naphthalene with molecular oxygen in the presence of a catalyst containing cobalt, manganese, bromine, and iron or copper in an acetic acid solvent to obtain 2,6-NDA in a high yield. The present inventors further conducted extensive research for improving the process of U.S. Pat. No. 4,886,906.

In the prior art, it has not been carried to control the oxygen concentration or the oxygen partial pressure in the exhaust gas in the processes for producing 2,6-NDA from 2,6-dimethyl naphthalene or 2,6-diisoprophyl naphthalene for increasing the yield of the reaction. However, it was known that the high oxygen concentration in the process is dangerous, and that the low oxygen concentration in the process is economical, and saves energy.

SUMMARY OF THE INVENTION

The present inventors found that the oxygen concentration or the oxygen partial pressure in the exhaust gas gives great effect on the yield of the product in the process, and that 2,6-NDA can be obtained by controlling the concentration or the partial pressure to a suitable value.

This invention relates to a process for producing 2,6-NDA which comprises oxidizing a 2-alkyl-6-acyl naphthalene with molecular oxygen-containing gas in the presence of a catalyst containing cobalt, manganese and bromine in an acetic acid solvent, characterized in that the oxygen concentration in the exhaust gas is controlled so as to satisfy following equation:

$$15/(X+7.5)+0.1 \leq Y \leq 90/(X+8)+0.4 \tag{1}$$

wherein Y is oxygen concentration (volume %) in the exhaust gas and X (cm) is distance from the inlet for an oxygen gas to the surface of the reaction solution in a static state.

PREFERABLE EMBODIMENTS (1) An aromatic polyvalent carboxylic acid in which at least two carboxylic acid groups are in an ortho-position may be used as a co-catalyst.

(2) Part of all of the mother liquor from which the 2,6-naphthalene dicarboxylic acid crystal has been separated may be cooled or concentrated and then cooled to remove the deposited impurities, and thereafter may be reused in the oxidation reaction.

(3) The catalyst may further contain iron, copper or a mixture thereof.

The above preferable embodiments (1)–(3) may be combined.

DETAILED DESCRIPTION OF THE INVENTION

Figure 1:
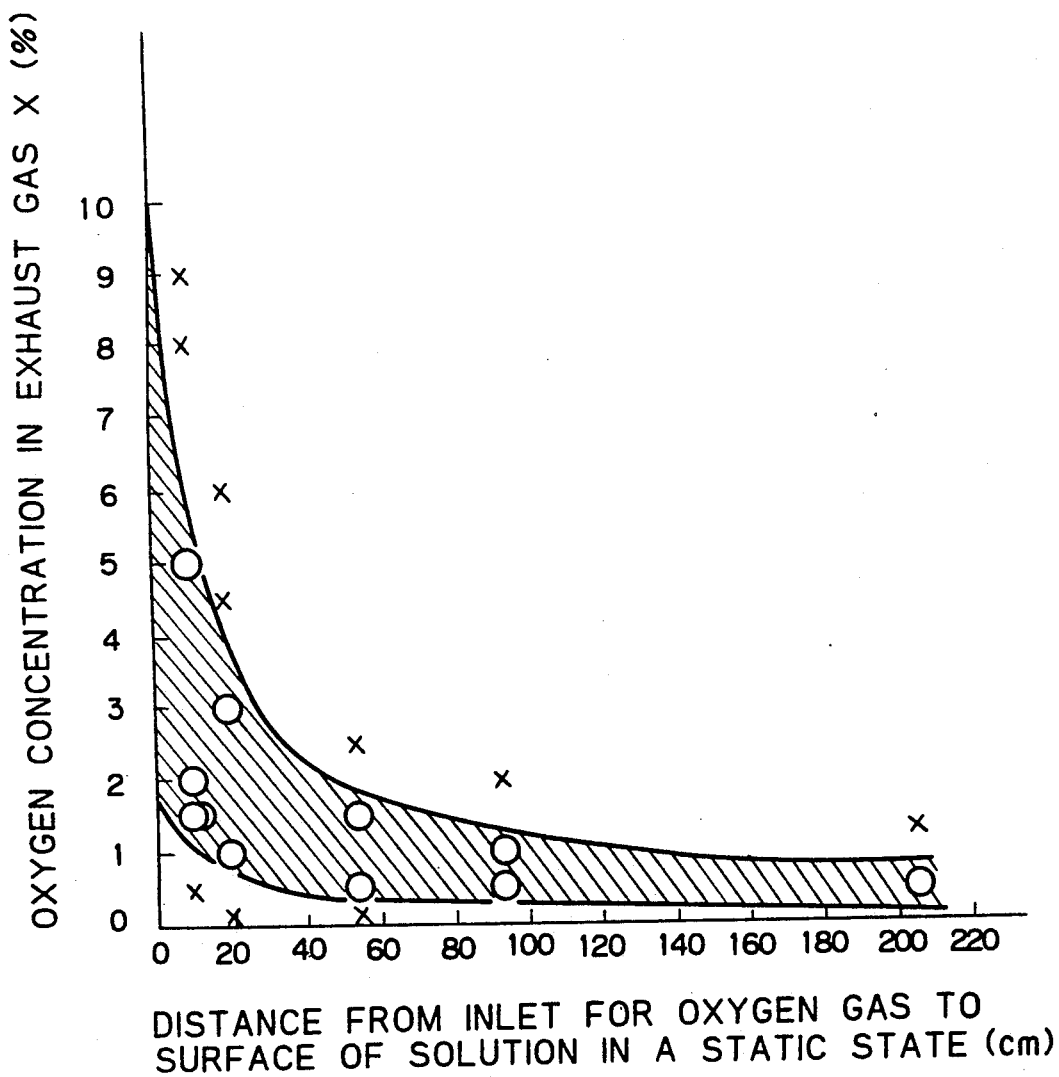
FIG. 1 is a graph showing the scope of the oxygen concentration to be controlled.

Examples of 2-alkyl-6-acyl naphthalenes include 2-methyl-6-acetyl naphthalene, 2-methyl-6-butyryl naphthalene, 2-ethyl-6-butyryl naphthalene and the like.

Acetic acid used as a solvent may contain small amounts of water formed by a reaction. The reaction mixture is in a slurry state after the reaction. So an adequate amount of acetic acid must therefore be used in order to allow the reaction product to be uniformly dispersed in the acetic acid. Usually, the amount of acetic acid used may be in the range of 2-10 times by weight, preferably 2.5-5 times by weight, of the 2-alkyl-6-acyl naphthalene.

It is preferable that the cobalt compounds and the manganese compounds used as the catalyst are dissolved in acetic acid under the reaction conditions. Aliphatic carboxylates such as cobalt acetate or manganese acetate; halides such as cobalt bromide or manganese bromide; oxides, hydroxides, carbonates; or acetyl acetate complexes of cobalt or manganese may be used as the cobalt compounds or manganese compounds. The concentration of the cobalt compound in acetic acid may be in the range of 0.06-1.0% by weight and preferably 0.1-0.5% by weight in terms of a cobalt atom. The concentration of the manganese compound in acetic acid may be in the range of 0.06-1.0% by weight and preferably 0.2-1.0% by weight in terms of a manganese atom. If the concentrations of cobalt or manganese are less than 0.06% by weight, the yield of 2,6-NDA is lowered. If the concentrations are more than 1.0% by weight, no increase in the yield of 2,6-NDA is achieved and the extra amount adds unnecessarily to the cost.

Bromine or bromine compounds may be used as the bromine component. Examples of the bromine compounds include inorganic bromine compounds such as bromine, sodium bromide, ammonium bromide, cobalt bromide and hydrogen bromide; and organic bromine compounds such as ethylene bromide and tetrabromoethane. The concentration of the bromine components in acetic acid may be in the range of 0.1-0.8% by weight and preferably 0.1-0.5% by weight in terms of a bromine atom. When the concentration of the bromine component is less than 0.1% by weight, the yield of 2,6-NDA is lowered. If the concentration is more than 0.8% by weight, the solution causes corrosion of the piping and the vessel.

The iron component and/or the copper component which may be used as an optional components are capable of forming metal ion in the reaction system. Examples of suitable iron components include iron power, iron chlorides, iron bromides, iron acetates and the like. Examples of suitable copper components include copper powder, copper sulfate, copper acetate, copper chloride, copper bromide and the like. The concentration of the iron component in acetic acid may be in the range of 0.01-0.5% by weight, preferably 0.03-0.1% by weight, in terms of an iron atom. The concentration of the copper component in acetic acid may be in the range of 0.001-0.2% by weight, preferably 0.02-0.05% by weight, in terms of a copper atom. If the concentration of the iron component is less than 0.01% by weight or when the concentration of the copper component is less than 0.001% by weight, the activity of by-reactions is increased and the yield of 2,6NDA is reduced. If the concentration of the iron component is more than 0.5% by weight or the concentration of the copper component is more than 0.2% by weight, no further increase in the yield of 2,6NDA is achieved.

Examples of a suitable molecular oxygen-containing gas include air and a mixture of nitrogen and oxygen.

The reaction temperature may be in the range of 180° C.-220° C., preferably 200° C.-210° C. If the reaction temperature is higher than 220° C., oxidation of acetic acid proceeds. If the temperature is lower than 180° C., the catalytic action is weakened, and the reactivity is therefore lowered.

The reaction is carried out at a pressure that is high enough to make the reaction system liquid.

The present process can be carried out by (i) a semi continuous method which comprises continuously introducing 2-alkyl-6-acyl naphthalene and the molecular oxygen-containing gas to a solution of the catalyst in acetic acid for a definite time or (ii) a continuous method which comprises continuously introducing the catalyst solution, 2-alkyl-6-acyl naphthalene and molecular oxygen-containing gas into a reaction vessel and continuously discharging the reaction mixture during the reaction.

The features of the present invention lie in specifying the lower limit and the upper limit of the oxygen concentration in the exhaust gas. If the reaction is carried out in excess of the upper limit, the yield of the oxidation is strikingly decreased. If the reaction is carried out below the lower limit, the atmosphere of oxygen shortage is formed, whereby the quality and the yield of 2,6-NDA are lowered. That is, the reaction is carried out so as to satisfy the following equation:

$$15/(X+7.5)+0.1 \leq Y \leq 90/(X+8)+0.4 \qquad (1)$$

The oxygen concentration in the exhaust gas can be measured by analyzing the gas withdrawn from the exit for exhaust gas through reflux condenser. The distance from the inlet for an oxygen gas in the vessel to the surface of the reaction solution is measured in a static state or the state in which stirring operation and blowing of oxygen are not carried out. The distance can also be derived by calculation.

In FIG. 1, symbol, O shows the oxygen concentration inside the present invention, whereas symbol, X shows the oxygen concentration outside the present invention. That is, the scope of the present invention is shown in diagonal lines.

The catalyst of the present invention may contain iron, copper or mixture thereof. The catalyst may also contain an aromatic polyvalent carboxylic acid in which at least two carboxylic acid groups are in an ortho-position or its precursor with or without iron or copper.

Examples of the polyvalent carboxylic acids include trimellitic acid, pyromellitic acid and phthalic acid. Since dimethyl benzaldehyde, trimethyl benzaldehyde and the like are likely to be oxidized in the presence of cobalt, manganese and bromine to form the polyvalent carboxylic acid, these compounds can be used as the precursor.

The amount of the aromatic polyvalent carboxylic acid or its precursor used may be in the range of 0.05-5% by weight, and preferably 0.1-3% by weight. If the amount of the carboxylic acid or its precursor is less than 0.05% by weight, the yield of the product is low because of the lower effectiveness of the co-catalyst. If the amount of the carboxylic acid or its precursor is more than 5% by weight, much of the carboxylic acid is incorporated into the resuling 2,6-NDA after purification.

In our experience at the oxidation of paraxylene, metaxylene, dimethyl-benze-aldehyde, or trimethyl-benzealdehyde, the carboxylic acid bonds to a manganese ion to form a stable complex, thereby impairing the function of manganese. So the aromatic polycarboxylic acid was thought to be one of impurities. Therefore, if the aromatic polyvalent carboxylic acid is used, the amount of manganese used depends on the amount of the carboxylic acid used. The relationship between the amount of Mn and the amount of the carboxylic acid is as follows:

$$54.94A(X'/M) \leq Y' \leq 219.76A(X'/M) \quad (2)$$

wherein $Y'$ is the concentration (% by weight) of manganese in an acetic acid solvent; $X'$ is the concentration (% by weight) of the aromatic polyvalent carboxylic acid or its precursor in the acetic acid solvent; M is the molecular weight of the carboxylic acid; and A is the number of adjacent carboxylic acid groups of the carboxylic acid. For example, A is 1 in phthalic acid or trimellitic acid, and A is 2 in pyromellitic acid.

According to preferable embodiment of the present invention, the amount of manganese is in excess of the equivalent of manganese which can bond to the aromatic polyvalent carboxylic acid to form a stable complex is used, and therefore, the yield of 2,6-NDA is strikingly increased. If the concentration of manganese is less than $54.94A(X'/M)$, the oxidation reaction is strikingly impaired, and as a result the yield of 2,6-NDA is lowered. If the concentration of manganese is more than $219.76A(X'/M)$, the yield of 2,6-NDA is not increased. The extra amount adds unnecessarily to the cost.

The reason why the yield of 2,6-NDA is strikingly increased by using the amount of the manganese in excess of the equivalent of manganese which can bond to the aromatic polyvalent carboxylic acid to form a stable complex is thought to be that though most of the aromatic polyvalent carboxylic acid forms a complex with the manganese, part of the carboxylic acid which converts to anion, allows oxidation-reduction potential of free manganese to exist and suppresses the by-reaction, and as a result, yield of 2,6-NDA is increased.

The aromatic polyvalent carboxylic acid may be directly added to the solvent. Alternatively, the solution such as the mother liquor containing the carboxylic acid may be added to the solvent.

As mentioned, a precursor such as dimethyl benzaldehyde, trimethyl benzaldehyde or the like which easily convert to the aromatic polyvalent carboxylic acid by oxidation may be added to the solvent.

After the oxidation reaction is completed, the slurry of the reaction mixture is cooled to 80° C. to crystallize the product, 2,6-NDA. The 2,6-NDA crystals are separated from the mother liquor by filtration. In conventional industrial operations, a catalyst and a solvent are added to the resulting mother liquor as occasion demands and part of water is removed from the mixture, and then the mixture is recirculated to the reaction system. In this recycling operation, intermediates, by-products and impurities in the raw material are recirculated to the reaction system. In addition, derivatives or isomers of 2-alkyl-6-acyl naphthalene is contained in the raw material. Therefore, purity of the product is gradually lowered in conventional recirculating methods.

According to preferable embodiment (2) of the present invention, the mother liquor separated from the 2,6-NDA crystals after the oxidation reaction is cooled, or concentrated and cooled, thereby precipitating the impurities and removing the impurities. Therefore, purity of the resulting product is not lowered, and decreasement in the yield of 2,6-NDA and precipitation of the impurities in the product can be avoided.

When the concentration of impurities in the mother liquor is more than 5% by weight, the impurities can be precipitated by cooling the mother liquor as it is. However, when the concentration of impurities is less than 5% by weight, the mother liquor is concentrated by heating it, and then the impurities are precipitated. Preferably, the cooling temperature should be as low as possible. The cooling temperature depends on the degree of concentration. If the concentration is not carried out, the cooling temperature is in the range of 10°–20° C. If the liquor is concentrated to one second, the cooling temperature is in the range of 20°–30° C. If the liquor is concentrated to one fourth, the cooling temperature is in the range of 50°–60° C. The amount of the mother liquor recirculated depends on the quality of the product. That is, if the product in a high purity is required, 60–80% of the mother liquor is recirculated. If not, 75–90% of the liquor is recirculated.

The starting material can be obtained by acylating a commercially available 2-alkyl naphthalene. Since highly pure 2,6-NDA can be obtained from the starting material, a 2-alkyl-6-acyl naphthalene, the present invention is industrially significant.

This invention is further explained by way of the following non-limiting examples and control runs. All percentages and parts are on a weight basis, unless specified otherwise.

Examples 1–11 and Control Runs 1–10 relate to the present invention (claim 1); Examples 12–20 and Control Run 11 relate to preferable embodiment (1) of the present invention; and Examples 21–23 and Control Runs 12–13 relate to preferable embodiment (2) of the present invention.

EXAMPLE 1

The following components were charged into a 500 ml titanium autoclave equipped with reflux condenser, stirring apparatus, heating apparatus, an inlet for raw material, an inlet for gas and an exit for exhaust gas:

| | |
|---|---|
| acetic acid | 150 g |
| cobalt acetate tetrahydrate | 1.26 g (Co 0.20%) |
| manganese acetate tetrahydrate | 1.33 g (Mn 0.20%) |
| hydrobromic acid (47%) | 1.61 g (Br 0.50%) |
| iron powder | 0.15 g (Fe 0.10%) |

The concentration of Co, Mn, Br and Fe are based on weight of acetic acid. A nitrogen gas was introduced from the inlet for gas to 10 kg/cm²G, and the mixture was heated to 220° C. and 21 kg/cm²G. The nitrogen was replaced by compressed air introduced from the inlet. The mixture was violently stirred while blowing compressed air. 2-methyl-6-butyryl naphthalene which had been heated to about 60° C. was introduced at a rate of 0.5 g/min for 1 hour from the inlet for raw material by pump. The amount of air introduced was controlled so that the concentration of oxygen in the exhaust gas amounted to 2%. After introduction of the starting material was completed, the blowing of air was continued for addition 10 minutes, the reaction was allowed to be completed. Then, the distance between the inlet for gas and the surface of the liquid in a static state was 9 cm. The autoclave was cooled and open. The reaction product slurry was obtained. The crystals were separated from the liquid by filtration. The resulting crystals were washed with acetic acid and dried. The gas-chromatograph analysis of the resulting crystals and 2,6-NDA, oxidation intermediates and by-products in the mother liquor showed that the yield of 2,6-NDA having purity of 99.0% was 27.63 g. The yield of 2,6-

NDA containing 2,6-NDA in the mother liquor was 89.5 mol%.

EXAMPLE 2

The procedure of Example 1 was repeated except that the oxygen concentration in the exhaust gas was 5%. The yield of the resulting 2,6-NDA was 83 mol % and the purity thereof was 98.2%.

CONTROL RUN 1

The procedure of Example 1 was repeated except that the compressed air was introduced so that the oxygen concentration amounted to 8%. The yield of the resulting 2,6-NDA was 73.4 mol % and the purity thereof was 95.3%.

EXAMPLE 3

The procedure of Example 1 was repeated except that a mixture of nitrogen and oxygen containing 13% of oxygen was used as an oxidation gas and the mixture was introduced into the autoclave at the same rate as the rate of air introduced in Control Run 1. The oxygen concentration in the exhaust gas was 1.5%. The yield of the resulting 2,6-NDA was 82.2 mol % and the purity thereof was 98.5%.

CONTROL RUN 2

The procedure of Example 1 was repeated except that the compressed air was introduced so that the oxygen concentration in the exhaust gas amounted to 0.5%. 24.5 g of 2,6-NDA having purity of 91% was obtained. The yield and the purity of the resulting 2,6-NDA were 73.4 mol % and 94.4%, respectively.

EXAMPLE 4

The following components were charged into a 3 l titanium autoclave equipped with reflux condenser, stirring apparatus, heating apparatus, an inlet for raw material, an inlet for gas and an exit for exhaust gas:

| | |
|---|---|
| acetic acid | 1200 g |
| cobalt acetate tetrahydrate | 10.14 g (Co 0.20%) |
| manganese acetate tetrahydrate | 10.71 g (Mn 0.20%) |
| ferrous bromide (50% aqueous solution) | 12.70 g (Fe 0.10%) |
| hydrobromic acid (47%) | 8.11 g (Br 0.60%) |

The concentration of Co, Mn, Br and Fe are based on weight of acetic acid. A nitrogen gas was introduced from the inlet to 10 kg/cm$^2$G, and the mixture was heated to 220° C. and 21 kg/cm$^2$G. The nitrogen was replaced by compressed air introduced from the inlet. The mixture was violently stirred while blowing air. 2-methyl-6-butyryl naphthalene which had been heated to about 60° C. was introduced at a rate of 2.5 g/min for 1 hour from the inlet for raw material by pump. The amount of air introduced was controlled so that the concentration of oxygen in the exhaust gas amounted to 1%. After introduction of the starting material was completed, the blowing of air was continued for addition 10 minutes, the reaction was allowed to be completed. Then, the distance between the inlet for gas and the surface of the liquid in a static state was 19 cm. The resulting product was treated as in Example 1. The yield and the purity of 2,6-NDA were 88.1 mol % and 99.5%, respectively.

EXAMPLE 5

The procedure of Example 4 was repeated except that the oxygen concentration in the exhaust gas was 3%. The yield of the resulting 2,6-NDA was 87.3 mol % and the purity thereof was 99.2%.

CONTROL RUN 3

The procedure of Example 4 was repeated except that the compressed air was introduced so that the oxygen concentration in the exhaust gas amount to 4.5%. The yield of the resulting 2,6-NDA was 79.1 mol % and the purity thereof was 95.0%.

CONTROL RUN 4

The procedure of Example 4 was repeated except that the compressed air was introduced so that the oxygen concentration in the exhaust gas amounted to 6%. The yield of 2,6-NDA was 76.6 mol %. The purity thereof was 93.7%.

CONTROL RUN 5

The procedure of Example 4 was repeated except that the compressed air was introduced so that the oxygen concentration in the exhaust gas amounted to 0.1%. The yield and the purity of the resulting 2,6-NDA were 73.2 mol % and 92.1%, respectively.

EXAMPLE 6

The following components were charged into a 6 l zirconium autoclave equipped with reflux condenser, stirring apparatus, heating apparatus, an inlet for raw material, an inlet for gas and an exit for exhaust gas:

| | |
|---|---|
| acetic acid | 3000 g |
| cobalt acetate tetrahydrate | 38.04 g (Co 0.30%) |
| manganese acetate tetrahydrate | 40.14 g (Mn 0.30%) |
| ferrous bromide (50% aqueous solution) | 23.16 g (Fe 0.10%) |
| hydrobromic acid (47%) | 20.28 g (Br 0.60%) |

The concentration of Co, Mn, Br and Fe are based on weight of acetic acid. A nitrogen gas was introduced from the inlet, and the mixture was heated to 210° C. The mixture of 7 parts of the catalyst solution having the same proportion as the above catalyst solution and 1 part of 2-methyl-6-butyryl naphthalene was introduced at a rate of 2000 g/hr under a pressure from the inlet for raw material with stirring while introducing air into the autoclave. At the same time the resulting product solution was withdrawn so that the surface of the solution was kept constantly. The operation was continued for 6 hours. The amount of air introduced was controlled so that the oxygen concentration in the exhaust gas amounted to 0.5%. After the introduction of the mixed solution was discontinued, air was introduced for additional 10 minutes to allow the oxidation reaction to be continued. Then, the distance between the inlet for gas and the surface of the liquid in a static state was 54 cm. The resulting product was treated as in Example 1. The yield and the purity of 2,6-NDA were 87.7 mol % and 98.8%, respectively.

EXAMPLE 7

The procedure of Example 6 was repeated except that the oxygen concentration in the exhaust gas was 1.5%. The yield of the resulting 2,6-NDA was 84.3 mol % and the purity thereof was 99.0%.

CONTROL RUN 6

The procedure of Example 6 was repeated except that the compressed air was introduced so that the oxygen concentration amounted to 2.5%. The yield of the resulting 2,6-NDA was 79.0 mol % and the purity thereof was 95.5%.

CONTROL RUN 7

The procedure of Example 6 was repeated except that the compressed air was introduced so that the oxygen concentration amounted to 0.1%. The yield of the resulting 2,6-NDA was 77.3 mol % and the purity thereof was 94.5%.

EXAMPLE 8

The following components were charged into a 12 l zirconium autoclave equipped with reflux condenser, stirring apparatus, heating apparatus, an inlet for raw material, an inlet for gas and an exit for exhaust gas:

| acetic acid | 7000 g |
| --- | --- |
| cobalt acetate tetrahydrate | 88.80 g (Co 0.30%) |
| manganese acetate tetrahydrate | 93.71 g (Mn 0.30%) |
| ferrous bromide (50% aqueous solution) | 54.10 g (Fe 0.10%) |
| hydrobromic acid (47%) | 69.90 g (Br 0.75%) |

The concentration of Co, Mn, Br and Fe are based on weight of acetic acid. A nitrogen gas was introduced from the inlet to 10 kg/cm$^2$G, and the mixture was heated to 210° C. and 20 kg/cm$^2$G. The nitrogen was replaced by compressed air introduced from the inlet. The mixture was violently stirred while compressed blowing air. 2-methyl-6-butyryl naphthalene which had been heated to about 60° C. was introduced at a rate of 500 g/hr for 2 hours from the inlet for raw material by pump. The amount of air introduced was controlled so that the concentration of oxygen in the exhaust gas amounted to 0.5%. After introduction of the starting material was completed, the blowing of air was continued for addition 10 minutes, the reaction was allowed to be completed. Then, the distance between the inlet for gas and the surface of the liquid in a static state was 93 cm. The resulting product was treated as in Example 1. The yield and the purity of 2,6-NDA were 86.0 mol % and 98.9%, respectively.

EXAMPLE 9

The procedure of Example 8 was repeated except that the oxygen concentration in the exhaust gas was 1%. The yield of the resulting 2,6-NDA was 85.0 mol % and the purity thereof was 98.8%.

CONTROL RUN 8

The procedure of Example 8 was repeated except that the compressed air was introduced so that the oxygen concentration in the exhaust gas amounted to 2%. The yield and the purity of the resulting 2,6-NDA were 79.8 mol % and 95.8%, respectively.

EXAMPLE 10

The following components were charged into a 15 m$^3$ titanium-clad high pressure reactor equipped with reflux condenser, stirring apparatus, heating apparatus, an inlet for raw material, an inlet for gas and an exit for exhaust gas:

| acetic acid | 1000 kg |
| --- | --- |
| cobalt acetate tetrahydrate | 12.68 kg (Co 0.30%) |
| manganese acetate tetrahydrate | 13.38 kg (Mn 0.30%) |
| ferrous bromide (50% aqueous solution) | 7.72 kg (Fe 0.10%) |
| hydrobromic acid (47%) | 6.76 kg (Br 0.60%) |

The concentration of Co, Mn, Br and Fe are based on weight of acetic acid. A nitrogen gas was introduced from the inlet to 10 kg/cm$^2$G, and the mixture was heated to 210° C. and 20 kg/cm$^2$G. The nitrogen was replaced by compressed air introduced from the inlet. The mixture was violently stirred while compressed blowing air. 2-methyl-6-butyryl naphthalene which had been heated to about 60° C. was introduced at a rate of 250 kg/hr for 4 hours from the inlet for raw material by pump. The amount of air introduced was controlled so that the concentration of oxygen in the exhaust gas amounted to 0.5%. After introduction of the starting material was completed, the blowing of air was continued for additional 10 minutes, the reaction was allowed to be completed. Then, the distance between the inlet for gas and the surface of the liquid in a static state was 205 cm. The resulting product was treated as in Example 1. The yield and the purity of 2,6-NDA were 87.3 mol % and 97.9%. respectively.

CONTROL RUN 9

The procedure of Example 10 was repeated except that the compressed air was introduced so that the oxygen concentration in the exhaust gas amounted to 1.3%. The yield and the purity of the resulting 2,6-NDA were 78.8 mol % and 94.5%, respectively.

EXAMPLE 11

The following components were charged into the autoclave of Example 1:

| acetic acid | 150 g |
| --- | --- |
| cobalt acetate tetrahydrate | 0.250 g (Co 0.04%) |
| manganese acetate tetrahydrate | 1.270 g (Mn 0.19%) |
| hydrobromic acid (47%) | 0.04 g (Br 0.015%) |

The concentration of Co, Mn and Br are based on weight of acetic acid. A nitrogen gas was introduced from the inlet for gas to 10 kg/cm$^2$G, and the mixture was heated to 200° C. and 19 kg/cm$^2$G. The nitrogen was replaced by compressed air introduced from the inlet. The mixture was violently stirred while blowing compressed air. 2-methyl-6-acetyl naphthalene which had been heated to about 60° C. was introduced at a rate of 0.5 g/min for 1 hour from the inlet for raw material by pump. The amount of air introduced was controlled so that the concentration of oxygen in the exhaust gas amounted to 1.5%. After introduction of the starting material was completed, the blowing of air was continued for addition 10 minutes, the reaction was allowed to be completed. Then, the distance between the inlet for gas and the surface of the liquid in a static state was 9 cm. The resulting product was treated as in Example 1. The yield and the purity of 2,6-NDA were 84.2 mol % and 99.5%, respectively.

CONTROL RUN 10

The procedure of Example 11 was repeated except that the compressed air was introduced so that the oxygen concentration in the exhaust gas amounted to 9%.

The yield and the purity of the resulting 2,6-NDA were 78.6 mol % and 93.9%, respectively.

In FIG. 1, the vertical axis relates to oxygen concentration Y (% by volume) in exhaust gas and horizontal axis relates to distance (cm) between inlet for oxidation gas and surface of reaction solution in a static state. Symbol O is inside the scope of the present invention and symbol X is outside the scope of the present invention. The scope of the present invention as shown in Equation (1) is shown in diagonal lines.

EXAMPLE 12

The following components were charged into a 2 l titanium autoclave equipped with reflux condenser, stirring apparatus, heating apparatus, inlet for raw material, inlet for gas and exit for exhaust gas:

| | | |
|---|---|---|
| acetic acid | 750 g | |
| cobalt acetate tetrahydrate | 6.34 g | (Co 0.20%) |
| manganese acetate tetrahydrate | 33.45 g | (Mn 1.00%) |
| ferrous bromide (50% aqueous solution) | 5.79 g | (Fe 0.10%) |
| hydrobromic acid (47%) | 3.45 g | (Br 0.60%) |
| trimellitic acid | 11.25 g | (1.5%) |

Each concentration is based on weight of acetic acid. A nitrogen gas was introduced from the inlet to 10 kg/cm²G, and the mixture was heated to 210° C. and 20 kg/cm²G. The nitrogen was replaced by compressed air introduced from the inlet. The mixture was violently stirred while blowing compressed air. 2-methyl-6-butyryl naphthalene having purity of 91.2% which had been heated to about 60° C. was introduced at a rate of 125 g/hr for 2 hours from the inlet for raw material by pump. The blowing of air was continued for additional 10 minutes, the reaction was allowed to be completed. The autoclave was cooled to 80° C. and open. The reaction product slurry was obtained. The crystals were separated from the liquid by filtration. The resulting crystals were washed with acetic acid and dried. The gas-chromatograph analysis of the resulting crystals and 2,6-NDA, oxidation intermediates and by-products in the mother liquor showed that the yield of 2,6-NDA containing 2,6-NDA in the mother liquor was 89.1 mol %.

CONTROL RUN 11

The procedure of Example 12 was repeated except that the manganese concentration was 0.2%. The yield of the resulting 2,6-NDA was 41.2 mol %.

EXAMPLE 13

The procedure of Example 12 was repeated except that trimellitic acid was not used. The yield of the resulting 2,6-NDA was 87.0 mol %.

EXAMPLE 14

The procedure of Example 12 was repeated except that the manganese concentration was 1.5% and trimellitic acid was not used. The yield of the resulting 2,6-NDA was 88.2 mol %.

EXAMPLE 15

The procedure of Example 12 was repeated except that pyromellitic acid (0.7%) was used instead of trimellitic acid. The yield of the resulting 2,6-NDA was 93.1 mol %.

EXAMPLE 16

The mother liquor containing trimellitic acid obtained in Control Run 12 was concentrated to 75%. A solvent and metal salts and bromine compounds shown in Example 12 were added to the concentrate, whereby 750 g of the catalyst solution having the same proportion as that in Example 12 was prepared. The concentration of trimellitic acid in the solution was 0.96%. 2-methyl-6-butyryl naphthalene was oxidized to 2,6-NDA by using the catalyst solution. The yield of 2,6-NDA was 93.8 mol %.

EXAMPLE 17

The following components were charged into the autoclave of Example 12:

| | | |
|---|---|---|
| acetic acid | 750 g | |
| cobalt acetate tetrahydrate | 9.51 g | (Co 0.30%) |
| manganese acetate tetrahydrate | 33.45 g | (Mn 1.00%) |
| ferrous bromide (50% aqueous solution) | 5.79 g | (Fe 0.10%) |
| hydrobromic acid (47%) | 3.45 g | (Br 0.50%) |

Each concentration is based on weight of acetic acid. A nitrogen gas was introduced from the inlet to 10 kg/cm²G, and the mixture was heated to 220° C. and 21 kg/cm²G. The nitrogen was replaced by compressed air introduced from the inlet. The mixture was violently stirred while blowing compressed air. A mixture of 250 parts of 2-methyl-6-butyryl naphthalene having purity of 85.5% which had been heated to about 60° C. and 8 parts of dimethyl benzaldehyde was introduced at a rate of 64.5 g/hr for 4 hours from the inlet for raw material by pump. After the introduction of the mixed solution was discontinued, the blowing of air was continued for additional 10 minutes, the reaction was allowed to be completed. The resulting product was treated as in Example 12. The yield of 2,6-NDA was 93.1 mol %.

EXAMPLE 18

The following components were charged into a 3 l zirconium autoclave equipped with reflux condenser, stirring apparatus, heating apparatus, inlet for raw material, inlet for gas and exit for product:

| | | |
|---|---|---|
| acetic acid | 1200 g | |
| cobalt acetate tetrahydrate | 15.21 g | (Co 0.30%) |
| manganese acetate tetrahydrate | 32.11 g | (Mn 0.60%) |
| ferrous bromide (50% aqueous solution) | 9.26 g | (Fe 0.10%) |
| hydrobromic acid (47%) | 5.52 g | (Br 0.50%) |
| trimellitic acid | 10.20 g | (0.85%) |

Each concentration is based on weight of acetic acid.

The autoclave was pressurized by a nitrogen gas. The mixture was heated to 210° C. A mixture of 4 parts of the above catalyst solution and 1 part of 2-methyl-6-butyryl naphthalene was introduced at a rate of 750 g/hr under a pressure with stirring while introducing air. At the same time, the resulting product solution was withdrawn so that the surface of the reaction solution was constantly kept. The operation was continued for 6 hours. After the introduction of the mixed solution was discontinued, air was introduced for additional 10 minutes to allow the reaction to be completed. The resulting product was treated as in Example 12. The yield of 2,6-NDA was 94.0 mol %.

EXAMPLE 19

The procedure of Example 18 was repeated except that trimellitic acid was not used. The yield of 2,6-NDA was 86.5 mol %.

EXAMPLE 20

The following components were charged into the autoclave of Example 12:

| | |
|---|---|
| acetic acid | 750 g |
| cobalt acetate tetrahydrate | 1.585 g (Co 0.05%) |
| manganese acetate tetrahydrate | 6.691 g (Mn 0.20%) |
| iron acetate (50% aqueous solution) | 0.128 g (Fe 0.05%) |
| sodium bromide | 0.773 g (Br 0.08%) |
| phthalic acid | 0.303 g (0.04%) |

Each concentration is based on weight of acetic acid.

The operation for initiating the reaction was carried out as in Example 12. When the autoclave was heated to 205° C., the nitrogen was replaced by compressed air introduced from the inlet. The mixture was violently stirred while blowing compressed air. 2-methyl-6-acetyl naphthalene having purity of 94.5% which had been heated to 50° C. was introduced at a rate of 110 g/hr for 1.5 hours from the inlet for raw material by pump. After the introduction of the reactant was discontinued, the blowing of air was continued for additional 10 minutes, the reaction was allowed to be completed. The resulting product was treated as in Example 12. The yield of 2,6-NDA was 92.1 mol %.

EXAMPLE 21

The following components were charged into a 2 l titanium autoclave equipped with reflux condenser, stirring apparatus, heating apparatus, inlet for raw material, inlet for gas, exit for gas and an exit for product:

| | |
|---|---|
| acetic acid | 750 g |
| cobalt acetate tetrahydrate | 6.34 g (Co 0.20%) |
| manganese acetate tetrahydrate | 6.69 g (Mn 0.20%) |
| ferrous bromide (50% aqueous solution) | 5.79 g (Fe 0.10%) |
| hydrobromic acid (47%) | 3.45 g (Br 0.60%) |

Each concentration is based on weight of acetic acid.

A nitrogen gas was introduced from the inlet to 10 kg/cm²G, and the mixture was heated to 210° C. and 20 kg/cm²G. The nitrogen was replaced by compressed air introduced from the inlet. The mixture was violently stirred while blowing compressed air. 2-methyl-6-butyryl naphthalene having purity of 91.2% which had been heated to about 60° C. was introduced at a rate of 125 g/hr for 2 hours from the inlet for raw material by pump. The blowing of air was continued for additional 10 minutes, the reaction was allowed to be completed. The autoclave was cooled to 80° C. and open. The reaction product slurry was obtained. The crystals were separated from the liquid by filtration. The resulting crystals were washed with acetic acid and dried. The gas-chromatograph analysis of the resulting crystal and 2,6-NDA, oxidation intermediates and by-products in the mother liquor showed that the yield and the purity of 2,6-NDA crystal were 88.3 mol % and 97.2%, respectively.

75 percent of the resulting mother liquor was concentrated one second and cooled to 25° C. The precipitate was removed from the mother liquor by filtration. To the concentrate were added the solvent, the bromine compounds and the above metal salts, so that the total amount of the solution amounted to 750 g and the proportion of the solution had the above-mentioned proportion. The above-mentioned operation was repeated to oxidize the 2-methyl-6-butyryl naphthalene.

The above operations were repeated 10 times. The yield and purity of 2,6-NDA in each operation are shown in Table 1.

CONTROL RUN 12

The procedure of Example 21 was repeated except that removal of the precipitate from the resulting mother liquor was not carried out. The results are shown in Table 1.

TABLE 1

| | Example 21 | | Control Run 12 | |
|---|---|---|---|---|
| times of recycles | purity of crystal | yield of 2,6-NDA | purity of crystal | yield of 2,6-NDA |
| 0 | 97.2 | 88.3 mol % | 98.1 | 87.9 mol % |
| 1 | 97.3 | 89.9 | 95.3 | 86.6 |
| 2 | 96.1 | 88.1 | 92.1 | 87.3 |
| 3 | 96.9 | 87.4 | 89.6 | 85.1 |
| 4 | 95.2 | 88.9 | 88.7 | 88.1 |
| 5 | 98.3 | 89.1 | 91.3 | 86.4 |
| 6 | 95.5 | 86.8 | 89.9 | 85.2 |
| 7 | 97.8 | 90.2 | 88.1 | 84.1 |
| 8 | 97.3 | 88.8 | 86.0 | 85.5 |
| 9 | 96.2 | 87.2 | 87.9 | 84.9 |
| 10 | 97.6 | 89.5 | 87.5 | 86.1 |

EXAMPLE 22

The following components were charged into the autoclave of Example 21:

| | |
|---|---|
| acetic acid | 750 g |
| cobalt acetate tetrahydrate | 9.51 g (Co 0.30%) |
| manganese acetate tetrahydrate | 10.03 g (Mn 0.30%) |
| ferrous bromide (50% aqueous solution) | 5.79 g (Fe 0.10%) |
| hydrobromic acid (47%) | 5.07 g (Br 0.60%) |

Each concentration is based on weight of acetic acid.

The mixture was heated to 210° C. while pressurizing the autoclave with a nitrogen gas. The mixed solution of 3 parts of the catalyst solution and 1 part of 2-methyl-6-butyryl naphthalene 91.2% pure was introduced at a rate of 125 g/hr under a pressure with stirring while introducing air. At the same time the resulting product solution was withdrawn so that the surface of the reaction solution was constantly kept. The above operation was continued for 6 hours.

The resulting product solution was separated into the crystals and the mother liquor. The resulting mother liquor was concentrated and cooled, and the precipitated impurities was removed from the mother liquor by filtration. To the concentrate were added the mixed solution of 3 parts of the catalyst solution and 1 part of the starting material. The recycling operation was continued for 40 hours. Then after the introduction of the mixed solution was discontinued, air was introduced into the solution for additional 10 minutes to allow the reaction to be completed.

The reaction product was treated as in Example 21. The yield of 2,6-NDA was 88.3 mol %. Its purity was 98.5%.

EXAMPLE 23

The following components were charged into the autoclave of Example 21:

| | |
|---|---|
| acetic acid | 750 g |
| cobalt acetate tetrahydrate | 9.51 g (Co 0.30%) |
| manganese acetate tetrahydrate | 10.03 g (Mn 0.30%) |
| ferrous bromide (50% aqueous solution) | 5.79 g (Fe 0.10%) |
| hydrobromic acid (47%) | 5.07 g (Br 0.60%) |

Each concentration is based on weight of acetic acid.

A nitrogen gas was introduced from the inlet to 10 kg/cm²G, and the mixture was heated to 205° C. and 15 kg/cm²G. The nitrogen was replaced by compressed air introduced from the inlet. The mixture was violently stirred while blowing compressed air. 2-methyl-6-butyryl naphthalene having purity of 85.5% which had been heated to about 60° C. was introduced at a rate of 108 g/hr for 2 hours from the inlet for raw material by means of pump. The blowing of air was continued for additional 10 minutes, the reaction was allowed to be completed. The autoclave was cooled to 80° C. and open. The reaction product slurry was obtained. The crystals were separated from the liquid by filtration. The resulting crystals were washed with acetic acid and dried. The gas-chromatograph analysis of the resulting crystals and 2,6-NDA, oxidation intermediates and by-products in the mother liquor showed that the yield and the purity of 2,6-NDA crystal containing 2,6-NDA in the mother liquor were 85.9 mol % and 95.8%, respectively.

75 percent of the resulting mother liquor was concentrated one second and cooled to 25° C. The precipitate was removed from the mother liquor by filtration. To the concentrate were added the solvent, the bromine compounds and the above metal salts, so that the total amount of the solution amounted to 750 g and the proportion of the solution had the above-mentioned proportion. After the solution was charged into the autoclave, the above-mentioned operation was repeated to oxidize the 2-methyl-6-butyryl naphthalene.

The above operations were repeated 4 times. The yield and purity of 2,6-NDA in each operation are shown in Table 2.

CONTROL RUN 13

The procedure of Example 23 was repeated except that removal of the precipitate from the resulting mother liquor was not carried out. The results are shown in Table 2.

TABLE 2

| times of recycles | Example 23 | | Control Run 13 | |
|---|---|---|---|---|
| | purity of crystal | yield of 2,6-NDA | purity of crystal | yield of 2,6-NDA |
| 0 | 95.8 | 85.9 mol % | 95.8 | 85.9 mol % |
| 1 | 93.4 | 83.5 | 89.9 | 80.3 |
| 2 | 94.0 | 81.9 | 83.8 | 78.4 |
| 3 | 92.9 | 80.2 | 85.8 | 74.7 |
| 4 | 93.5 | 82.0 | 84.2 | 75.2 |

What is claimed is:

1. A process for producing 2,6-naphthalene dicarboxylic acid which comprises oxidizing a 2-alkyl-6-acyl naphthalene with molecular oxygen-containing gas in the presence of a catalyst containing cobalt, manganese and bromine in an acetic acid solvent, characterized in that the oxygen concentration in the exhaust gas is controlled so as to satisfy the following equation:

$$15/(X+7.5)+0.1 \leq Y \leq 90/(X+8)+0.4 \quad (1)$$

wherein Y is oxygen concentration, volume %, in the exhaust gas and X, cm, is a distance between the inlet for an oxygen gas and the surface of the reaction solution in a static state.

2. The process of claim 1 wherein said catalyst further contains at least one metal selected from the group consisting of iron, copper and mixtures thereof.

3. The process of claim 1 wherein the catalyst further contains an aromatic polyvalent carboxylic acid in which at least two carboxylic acid groups are in an ortho-position or its precursor as a co-catalyst.

4. The process of claim 3 wherein the concentration of said aromatic polyvalent carboxylic acid or its precursor is 0.05–5% by weight, and the manganese concentration Y', % by volume, is as follows:

$$54.94A(X'/M) \leq Y' \leq 219.76A(X'/M) \quad (2)$$

wherein X' is the concentration, % by weight, of the aromatic polyvalent carboxylic acid or its precursor in the acetic acid solvent; M is the molecular weight of the carboxylic acid; A is the number of adjacent carboxylic acid groups in the carboxylic acid; and Y' is the concentration, % by weight, of manganese in an acetic acid solvent.

5. The process of claim 1 wherein the process further contains a step of separating the 2,6-naphthalene dicarboxylic acid crystals from the resulting reaction solution to form the 2,6-naphthalene dicarboxylic acid and the mother liquor.

6. The process of claim 5 wherein part of all of the mother liquor from which the 2,6-naphthalene dicarboxylic acid crystals have been separated is cooled, or concentrated and then cooled to remove the precipitated impurities, and thereafter is reused in the oxidation reaction.

* * * * *